United States Patent [19]
Chen et al.

[11] Patent Number: 5,856,492
[45] Date of Patent: Jan. 5, 1999

[54] EFFICIENT SYNTHESIS OF A CHIRAL MEDIATOR

[75] Inventors: Cheng Yi Chen, Colonia, N.J.; Feng Xu, Staten Island, N.Y.; Richard D. Tillyer, Westfield; Dalian Zhao, Fanwood, both of N.J.

[73] Assignee: Merck & Co., Inc., Rahway, N.J.

[21] Appl. No.: 2,853

[22] Filed: Jan. 5, 1998

Related U.S. Application Data

[60] Provisional application No. 60/034,926 Jan. 10, 1997 and provisional application No. 60/042,021 Apr. 17, 1997 and provisional application No. 60/045,167 Apr. 30, 1997.

[51] Int. Cl.⁶ .................. C07D 211/20; C07D 207/12
[52] U.S. Cl. .................. 546/185; 546/213; 546/248; 548/574; 548/951; 548/953
[58] Field of Search .................. 548/574, 951, 548/953; 546/185, 213, 248

[56] References Cited

U.S. PATENT DOCUMENTS

| | | |
|---|---|---|
| 2,552,502 | 5/1951 | Woodruff . |
| 2,723,269 | 11/1955 | Denton . |
| 2,975,193 | 3/1961 | Dice et al. . |
| 3,028,378 | 4/1962 | Testa et al. . |
| 3,468,893 | 9/1969 | Mizzoni . |
| 3,754,003 | 8/1973 | Pedrazzoli et al. . |

OTHER PUBLICATIONS

Azizov, et al., Chemical Abstract, No. 137905, 1987.
Amadji, et al., J. Am. Chem. Soc., vol. 118, pp. 12483–12484, 1996.
Ye, et al., Tetrahedron, vol. 50 (20), pp. 6109–6116, 1994.
Cox, et al., Tetrahedron: Asymmetry, vol. 2 (1), pp. 1–26, 1991.
Asami, et al., Tetrahedron: Asymmetry, vol. 5 (5), pp. 793–796, 1994.

*Primary Examiner*—Johann Richter
*Assistant Examiner*—Ebenezer Sackey
*Attorney, Agent, or Firm*—Valerie J. Camara; Mark R. Daniel

[57] ABSTRACT

An efficient method for the quantitative preparation and isolation of a compound of formula I

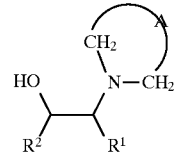

or its enantiomer, a chiral mediator used in enantioselective synthesis.

32 Claims, No Drawings

EFFICIENT SYNTHESIS OF A CHIRAL MEDIATOR

This application is a provisional application of 60/034,926, filed Jan. 10, 1997, 60/042,021 filed Apr. 17, 1997 and 60/045,167, filed Apr. 30, 1997.

BACKGROUND OF THE INVENTION

[R-(R*,S*)]-β-methyl-α-phenyl-1-pyrrolidineethanol, commonly referred to as (1R,2S)-N-pyrrolidinyl norephedrine, is an important chiral mediator for an enantioselective addition reaction, which is a key step in the synthesis of the reverse transcriptase inhibitor, (−)-6-chloro-4-cyclopropylethynyl-4-trifluoromethyl-1,4-dihydro-2H-3,1-benzoxazin-2-one, also known as DMP-266. As this chiral mediator is not commericially available, an efficient method for its preparation had to be developed.

The synthesis of DMP-266 and structurally similar reverse transcriptase inhibitors are disclosed in U.S. Pat. No. 5,519,021 and the corresponding PCT International Patent Application WO 95/20389, which published on Aug. 3, 1995. Additionally, the asymmetric synthesis of an enantiomeric benzoxazinone by a highly enatioselective acetylide addition and cyclization sequence has been described by Thompson, et al., Tetrahedron Letters 1995, 36, 937–940, as well as the PCT publication, WO 96/37457, which published on Nov. 28, 1996.

The use of chiral mediators has been disclosed in the published literature as useful in enatioselective synthesis, in inducing the enantioselectivity of additions to aldhydes, enantioselectivity of deprotonation of meso-epoxides and enantioselectivity of proton abstraction, etc. (See P. J. Cox and N. S. Simpkins, Tetrahedron: Asymmetry 1991, 2(1), 1–26; M., Asami, et al., Tetrahedron: Asymmetry 1994, 5(5), 793–6; M. Ye, et al., Tetrahedron, 1994, 50(20), 6109–16; and M. Amadji, et al. J. Am. Chem. Soc. 1996, 118, 12483–4.)

The instant invention discloses an efficient method for the quantitative preparation and isolation of the enantiomers of the compound of formula I

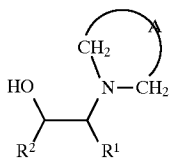

SUMMARY OF THE INVENTION

The present invention concerns a novel process for the preparation of a compound of formula I

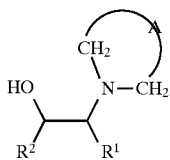

and its enantiomers. Additionally, the present invention also concerns compounds of Formula I as chiral mediators useful in enantioselective synthesis.

An example of a compound of Formula I is (1R,2S)-N-pyrrolidinyl norephedrine, which is a chiral mediator used in an enantioselective addition reaction. The preparation of [R-(R*,S*)]-β-methyl-α-phenyl-1-pyrrolidineethanol in quantitative yield was accomplished by alkylation of (1R,2S)-(−)-norephedrine with 1,4-dibromobutane in toluene using $NaHCO_3$ as base. The success of the reaction relied on the use of a suitable base such as $NaHCO_3$, and the efficient removal of water from the reaction media. The ([R-(R*,S*)]-β-methyl-α-phenyl-1-pyrrolidineethanol was isolated in 97% yield.

DETAILED DESCRIPTION OF THE INVENTION

The instant invention relates to a method for the preparation of a compound of Formula I

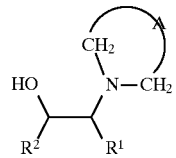

which represents a chiral mediator useful in the synthesis of the reverse transcriptase inhibitor, (−)-6-chloro-4-cyclopropylethynyl-4-trifluoromethyl-1,4-dihydro-2H-3,1-benzoxazin-2-one, also known as DMP-266.

A process for the preparation of a hydrochloride salt of a compound of Formula I

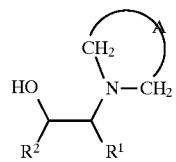

wherein

A represents:

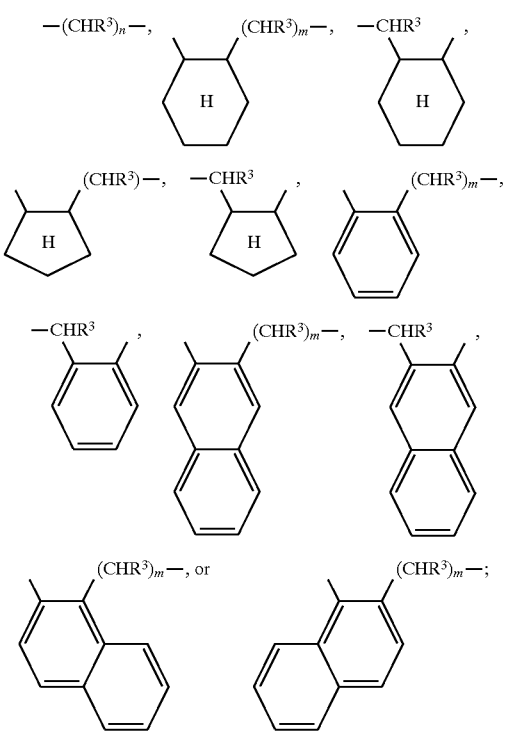

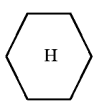

represents a six-membered ring, unsaturated or saturated, optionally substituted with one or two heteroatoms selected from N, O, or S, optionally substituted with $C_1$–$C_6$-alkyl;

represents: a five-membered ring, unsaturated or saturated, optionally substituted with one or two heteroatoms selected from N, O, or S, optionally substituted with $C_1$–$C_6$-alkyl;

n is 1, 2, or 3;
m is 0, or 1;
t is 0, 1, or 2;
s is 1 or 2;
$R^1$ is: H, phenyl, or $C_1$–$C_6$-alkyl, unsubstituted or substituted with $C_1$–$C_6$-alkoxy;
$R^2$ is: H, $C_1$–$C_6$-alkyl, or

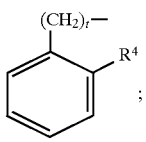

$R^3$ is: H, $C_1$–$C_6$-alkyl, or phenyl;
$R^4$ is: H, except that $R^1$ and $R^4$ can represent a carbon carbon bond, when t is 1 or 2, or —$(CH_2)_s$—, when t is 0;

comprising the steps of:
(a) refluxing the 1,2-amino alcohol compound,

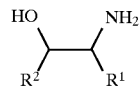

with an alkylating agent

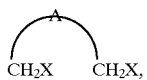

wherein X is Cl, Br, I, OTf, OTs or OMs; in the presence of a base and a solvent at a reaction temperature of about 65° to about 120° C. for reaction time of about 12 to about 36 hours, while removing the water formed to give a solution of crude compound of Formula I;

(b) adding hydrogen chloride in solution or as a gas to a solution of the crude compound of Formula I at about 10° to about 15° C. and maintaining a reaction temperature of about 10° to about 25° C. to form a slurry of the hydrochloride salt of the compound of Formula I;

(c) azeotropically distilling the solvents leaving a concentrated slurry-solution of the hydrochloride salt of the compound of Formula I;

(d) crystallizing the concentrated solution of the hydrochloride salt of the compound of Formula I at about 0° C. to about 20° C. to give a slurry of crystalline hydrochloride salt of the compound of Formula I; and (e) filtering the slurry of crystalline hydrochloride salt of the compound of Formula I to isolate crystalline hydrochloride salt of the compound of Formula I.

The process as recited above in step (a), wherein the base is selected from the group consisting of: $Li_2CO_3$, $Na_2CO_3$, $K_2CO_3$, $LiHCO_3$, $NaHCO_3$, $KHCO_3$, LiOH, NaOH, and KOH.

The process as recited above in step (a), wherein the solvent is selected from the group consisting of: toluene, heptane, n-butanol, methylcyclohexane, and tetrahydrofuran.

The process as recited above in step (a), wherein (1R,2S)-(−)-norephedrine to alkylating agent ratio is about a 1 to 1.1 ratio.

The process as recited above in step (a), wherein the dihalide to base ratio is about a 1 to 2 ratio.

The process as recited above in step (a), wherein the base is preferably $KHCO_3$, $NaHCO_3$, $K_2CO_3$, and $Na_2CO_3$.

The process as recited above in step (a), wherein the solvent system is toluene.

The process as recited above in step (a), wherein the reaction temperature is about 105° to about 118° C.

The process as recited above in step (a), wherein the reaction time is about 18 to about 24 hours.

The process as recited above wherein the compound of Formula I or its enantiomer is selected from the group consisting of:

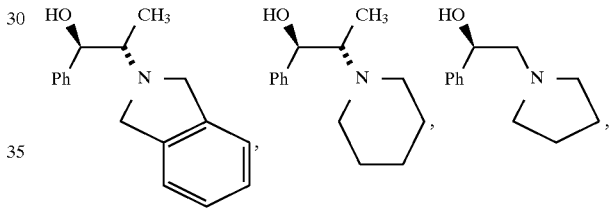

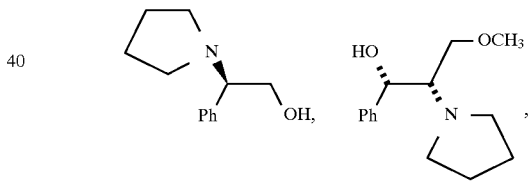

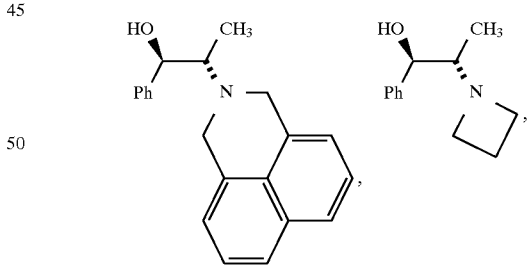

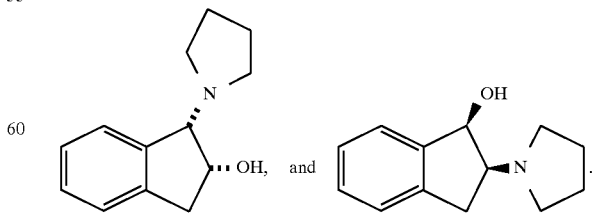

A process for the preparation of [R-(R*,S*)]-β-methyl-α-phenyl-1-pyrrolidineethanol hydrochloride or its enantiomer,

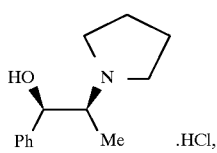

comprising the steps of (a) refluxing (1R,2S)-(–)-norephedrine or its enantiomer,

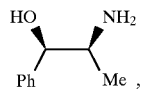

with 1,4-dibromobutane in the presence of a base, sodium bicarbonate and a solvent, toluene, at a reaction temperature of about 100° to about 120° C. for reaction time of about 12 to about 24 hours, while removing the water formed to give a toluene solution of crude [R-(R*,S*)]-β-methyl-α-phenyl-1-pyrrolidineethanol;

(b) adding a solution of hydrogen chloride in isopropanol to a toluene solution of [R-(R*,S*)]-β-methyl-α-phenyl-1-pyrrolidineethanol or its enantiomer at about 10° to about 15° C. and maintaining a reaction temperature of about 10° to about 25° C. to form [R-(R*,S*)]-β-methyl-α-phenyl-1-pyrrolidineethanol hydrochloride or its enantiomer;

(c) azeotropically distilling the isopropanol-toluene leaving a concentrated toluene slurry of [(R*,S*)]-β-methyl-α-phenyl-1-pyrrolidineethanol hydrochloride;

(d) crystallizing the concentrated toluene slurry of [R-(R*,S*)]-β-methyl-α-phenyl-1-pyrrolidineethanol hydrochloride or its enantiomer at about 0° C. to about 20° C. to give a toluene slurry of crystalline [R-(R*,S*)]-β-methyl-α-phenyl-1-pyrrolidineethanol hydrochloride; and (e) filtering the toluene slurry of crystalline [R-(R*,S*)]-β-methyl-α-phenyl-1-pyrrolidineethanol hydrochloride or its enantiomer to isolate crystalline [R-(R*,S*)]-β-methyl-α-phenyl-1-pyrrolidineethanol hydrochloride or its enantiomer.

The process as recited above in step (a), wherein (1R,2S)-norephedrine to 1,4-dibromobutane ratio is about a 1 to 1.1 ratio.

The process as recited above in step (a), wherein the 1,4-dibromobutane to $NaHCO_3$ is about a 1 to 2 ratio.

The process as recited above in step (a), wherein the reaction temperature is about 105° to about 118° C.

The process for the preparation of [R-(R*,S*)]-β-methyl-α-phenyl-1-pyrrolidineethanol or its enantiomer comprising the steps recited above and following additional steps:

(a) neutralizing [R-(R*,S*)]-β-methyl-α-phenyl-1-pyrrolidineethanol hydrochloride or its enantiomer with aqueous NaOH in toluene producing a biphasic solution containing [R-(R*,S*)]-β-methyl-α-phenyl-1-pyrrolidineethanol or its enantiomer;

(b) extracting [R-(R*,S*)]-β-methyl-α-phenyl-1-pyrrolidineethanol or its enantiomer into a toluene-organic layer; and (c) concentrating the [R-(R*,S*)]-β-methyl-α-phenyl-1-pyrrolidineethanol or its enantiomer containing toluene-organic layer to give solid [R-(R*,S*)]-β-methyl-α-phenyl-1-pyrrolidineethanol or its enantiomer.

A compound of Formula I:

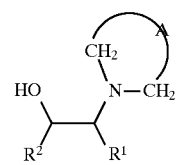

or its enantiomer, wherein

A represents:

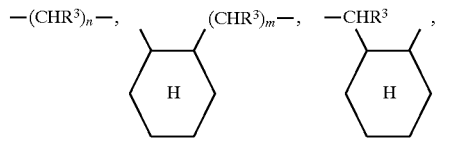

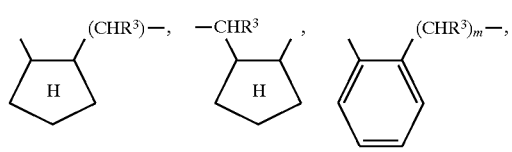

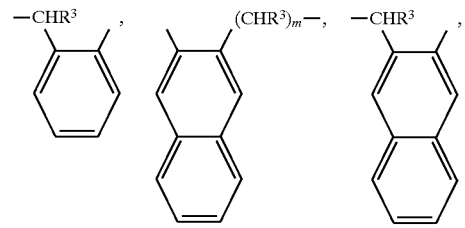

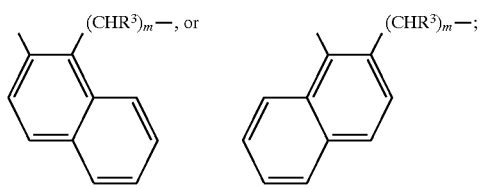

represents a six-membered ring, unsaturated or saturated, optionally substituted with one or two heteroatoms selected from N, O, or S, optionally substituted with $C_1$–$C_6$-alkyl;

represents: a five-membered ring, unsaturated or saturated, optionally substituted with one or two heteroatoms selected from N, O, or S, optionally substituted with $C_1$–$C_6$-alkyl;

n is 1, 2, or 3;

m is 0, or 1;

t is 0, 1, or 2;

s is 1 or 2;

$R^1$ is: H, phenyl, or $C_1$–$C_6$-alkyl, unsubstituted or substituted with $C_1$–$C_6$-alkoxy;

$R^2$ is: H, $C_1$–$C_6$-alkyl, or

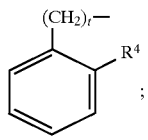

$R^3$ is: H, $C_1$–$C_6$-alkyl, or phenyl; and
$R^4$ is: H, except that $R^1$ and $R^4$ can represent a carbon carbon bond, when t is 1 or 2, or —$(CH_2)_s$—, when t is 0, with the proviso that:

(a) when the compound of structural formula I

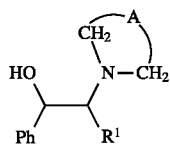 I or its enantiomer is defined as $R^1$ is H or $CH_3$, that A cannot represent —$(CHR^3)_n$—, or

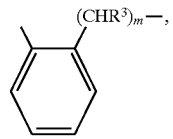

when n is 2, or 3, $R^3$ is H and m is 0; and (b) when the compound of structural formula I or its enantiomer is defined as

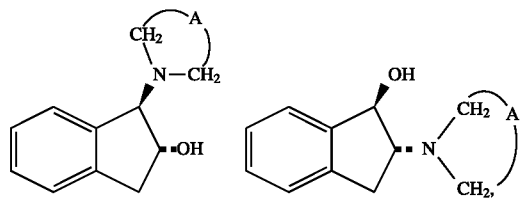

that A cannot represent —$(CHR^3)_n$—, when n is 2, and $R^3$ is H, as a free base or an acid salt thereof.

An acid salt such as a salt of an organic acid or inorganic acid. Examples of organic acids capable of forming an acid salt include but are not limited to: citric acid, acetic acid, trifluoroacetic acid, maleic acid, methanesulfonic acid, p-toluenesulfonic acid, formic acid, and benzoic acid. Examples of inorganic acids capable of forming an acid salt include but are not limited to: HCl, HBr, $H_3PO_4$ and $H_2SO_4$.

A further embodiment of this invention is the process for the preparation of a compound of Formula I:

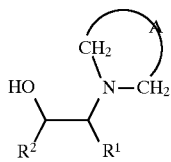 I wherein

A represents:

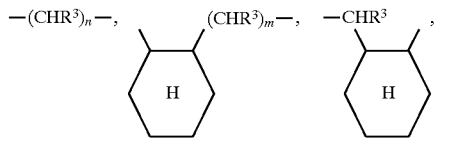

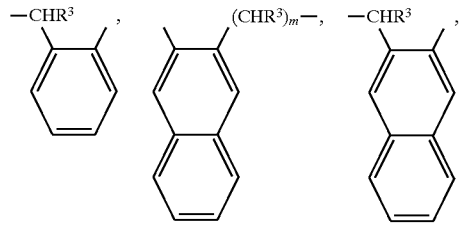

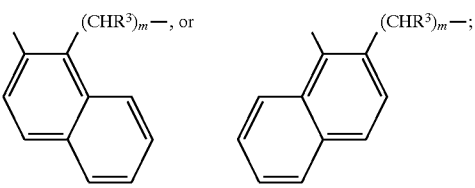

represents a six-membered ring, unsaturated or saturated, optionally substituted with one or two heteroatoms selected from N, O, or S, optionally substituted with $C_1$–$C_6$-alkyl;

represents: a five-membered ring, unsaturated or saturated, optionally substituted with one or two heteroatoms selected from N, O, or S, optionally substituted with $C_1$–$C_6$-alkyl;

n is 1, 2, or 3;
m is 0, or 1;
t is 0, 1, or 2;
s is 1 or 2;
$R^1$ is: H, phenyl, or $C_1$–$C_6$-alkyl, unsubstituted or substituted with $C_1$–$C_6$-alkoxy;
$R^2$ is: H, $C_1$–$C_6$-alkyl, or

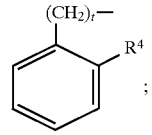

$R^3$ is: H, $C_1$–$C_6$-alkyl, or phenyl;
$R^4$ is: H, except that $R^1$ and $R^4$ can represent a carbon carbon bond, when t is 1 or 2, or —$(CH_2)_s$—, when t is 0;

comprising the steps of:
(a) refluxing the 1,2-amino alcohol compound,

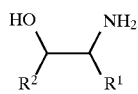

with an alkylating agent

wherein X is Cl, Br, I, OTf, OTs or OMs; in the presence of a base and a solvent at a reaction temperature of about 65° to about 120° C. for reaction time of about 12 to about 36 hours, while removing the water formed to give a solution of crude compound of Formula I;
(b) filtering the solvent solution containing the crude compound of Formula I to remove the sodium bromide salt, once the solution reaches room temperature;
(c) washing the sodium bromide wet cake with a solvent;
(d) extracting the filtrate-solvent solution containing the crude compound of Formula I with water to remove any additional sodium bromide salt;
(e) mixing the washed filtrate-solvent solution containing the crude compound of Formula I with an aqueous acid solution to form the acid salt of the compound of Formula I;
(f) isolating the aqueous layer containing the acid salt of a compound of Formula I;
(g) neutralizing a biphasic solution of the aqueous layer containing the acid salt of a compound of Formula I and solvent with a base while maintaining the temperature below about 30° C.;
(h) extracting the compound of Formula I from the biphasic solution into the solvent after mixing for less than about one hour; and
(i) isolating the solvent layer containing the compound of Formula I.

The process as recited above in steps (a) and (g), wherein the base used in each step is independently selected from the group consisting of: $Li_2CO_3$, $Na_2CO_3$, $K_2CO_3$, $LiHCO_3$, $NaHCO_3$, $KHCO_3$, LiOH, NaOH, and KOH.

The process as recited above in steps (a), (c) and (g) wherein the solvent is selected from the group consisting of: toluene, heptane, n-butanol, methylcyclohexane and tetrahydrofuran.

The process as recited above in step (e) wherein the aqueous acid solution is selected from the group consisting of: an aqueous inorganic acid solution and an aqueous organic acid solution.

The process as recited above in step (a) wherein aminoalcohol compound to dihalide ratio is about 1 to about 1.1 ratio.

The process as recited above in step (a) wherein the dihalide to base ratio is about 1 to about 2 ratio.

The process as recited above in step (a) wherein the base is selected from the group consisting of: $KHCO_3$, $NaHCO_3$, $K_2CO_3$, and $Na_2CO_3$.

The process as recited above in step (e) wherein the aqueous acid solution is an aqueous inorganic acid solution selected from the group consisting of: HCl, HBr, $H_3PO_4$ and $H_2SO_4$.

The process as recited above in step (e) wherein the aqueous acid solution is an aqueous organic acid solution selected from the group consisting of: citric acid, acetic acid, trifluoroacetic acid, maleic acid, methylsulfonic acid, p-toluenesulfonic acid, formic acid, and benzoic acid.

The process as recited above in steps (a), (c) and (g) wherein the solvent is toluene.

The process as recited above in step (a) wherein the reaction temperature is about 105° to about 118° C.

The process as recited above in step (a) wherein the reaction time is about 18 to about 24 hours.

The process as recited above in step (e) wherein the aqueous acid solution is citric acid.

The process as recited above in step (g) wherein the base is selected from the group consisting of: aqueous LiOH, KOH and NaOH.

The process as recited above wherein the compound of Formula I is selected from the group consisting of:

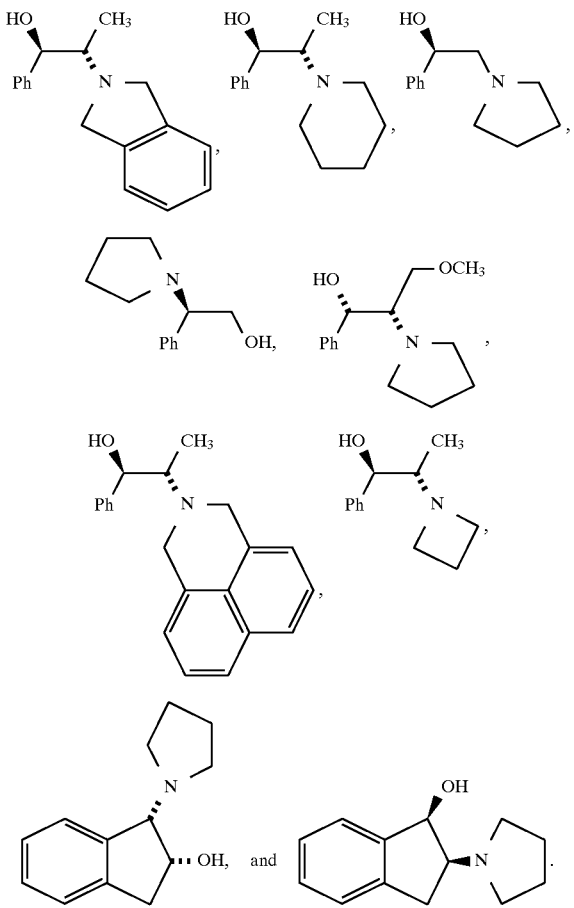

The process as recited above wherein the compound of Formula I is:

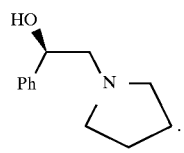

[R-(R*,S*)]-β-methyl-α-phenyl-1-pyrrolidineethanol, also referred to as (1R,2S)-N-pyrrolidinylnorephedrine, is an important chiral mediator for the enantioselective addition of an acetylide to a prochiral ketone. See Soai, K.; Yokoyama, S.; Hayasaka, T. *J. Org. Chem.* 1991, 4264. Niwa, S.; Soai, K. *J. Chem. Soc., Perkin Trans. I* 1990, 937;

and Thompson, A. S.; Corley, E. G.; Huntington, M. F., Grabowski, E. J. J. *Tetra. Lett.* 1995, 36, 8937. This reaction has been successfully applied to the synthesis of the reverse transcriptase inhibitor L-743,726 (DMP-266) (Scheme 1). See A. S. Thompson, et al. *Tetra. Lett.* 1995, 36, 8937. [R-(R*,S*)]-β-methyl-α-phenyl-1-pyrrolidineethanol has been synthesized from norephedrine and 1,4-dibromobutane in aqueous n-butanol using $K_2CO_3$ as base. The reaction formed several undesired impurities and the final isolated product yield was only 75%. The preparation of another similar compound, (1S,2R )-N-pyrrolidinylnorephedrine, has been reported. See K. Soai, et al., T. *J. Org. Chem.* 1991, 4264. S. Niwa, et al. *J.Chem. Soc., Perkin Trans. I* 1990, 937. The method used $K_2CO_3$ as base, and the yield of the product was only 33%. We have recently found that the reaction was extremely efficient when it was run in toluene using $NaHCO_3$ as base which gave ([R-(R*,S*)]-β-methyl-α-phenyl-1-pyrrolidineethanol quantitatively. (The syntheses of pyrrolidinyl alkanols using $NaHCO_3$ as a base was reported to give pyrrolidinyl derivatives in moderate yields. See Moffett, R. B. *J. Org. Chem.* 1949, 862. ) Enantioselectivity of 2 (up to 99% ee) was achieved when the toluene solution of [R-(R*,S*)]-β-methyl-α-phenyl-1-pyrrolidineethanol was used in the addition reaction of cyclopropylacetylide to the PMB-protected ketoaniline 1.

Scheme 1

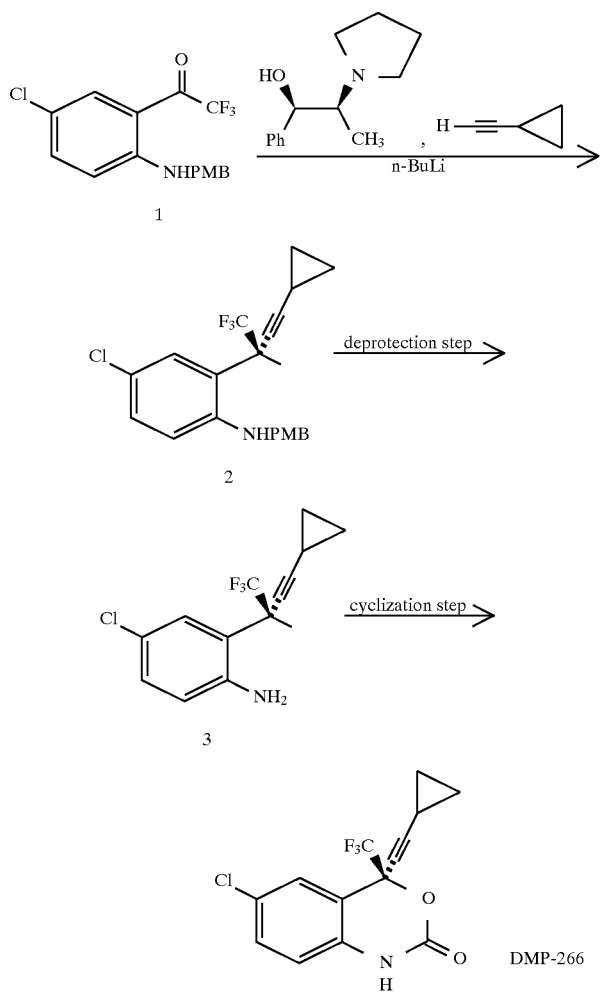

The instant invention describes a method for the preparation of a compound of formula I

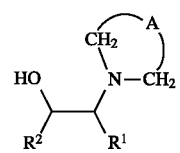

which as discussed above is useful as a chiral mediator in the addition reaction outlined in Scheme 1.

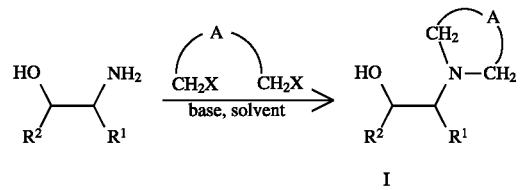

Examples of the alkylating agent useful in this method are: 1,3-dibromopropane, 1,4-dibromobutane, 1,5-dibromopentane, (2-bromomethyl)benzylbromide, 2-(2-bromoethyl)benzylbromide, 1,2-di(bromomethyl) naphthalene, 2,3-di(bromomethyl)naphthalene, 1,8-di (bromomethyl)naphthalene, etc. Additionally, representative heterocyclic alkylating agents are: [2,3-di(bromomethyl)] pyridine, [3,4-di(bromomethyl)]-pyridine, 2-(2-bromoethyl) -3-bromomethylpyridine, 3-(2-bromoethyl)-2-bromomethylpyridine, 3-(2-bromoethyl)-4-bromomethylpyridine, 4-(2-bromoethyl)-3-bromomethylpyridine, 3-(2-bromoethyl)-4-bromomethyl-pyridine, etc. Also included are the chloride, iodide, tosylate, mesylate and triflate analogs of the aforementioned alkylating agents. (Note: OTs represents tosylate; OMs represents mesylate and OTf represents triflate).

The bases useful in this method are: $Li_2CO_3$, $Na_2CO_3$, $K_2CO_3$, $LiHCO_3$, $NaHCO_3$, $KHCO_3$, LiOH, NaOH, and KOH. The solvent systems useful in this method are: toluene, heptane, n-butanol, tetrahydrofuran. The preferred base-solvent system was $NaHCO_3$-toluene, which allowed for the isolation of the chiral mediator in crystalline form in qualitative yield.

The chiral mediator produced is easier to handle as the salt form. Also within the scope of this invention are the salts of the compound of formula I:

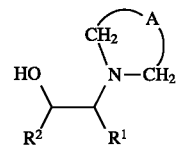

The actual compound used in the chiral addition reaction is the free base, which is generated in situ prior to use in the addition reaction.

The following examples are meant to be illustrative of the present invention. These examples are presented to exemplify the invention and are not to be construed as limiting the scope of the invention.

EXAMPLE 1

[R-(R*,S*)]-β-Methyl-α-phenyl-1-pyrrolidineethanol

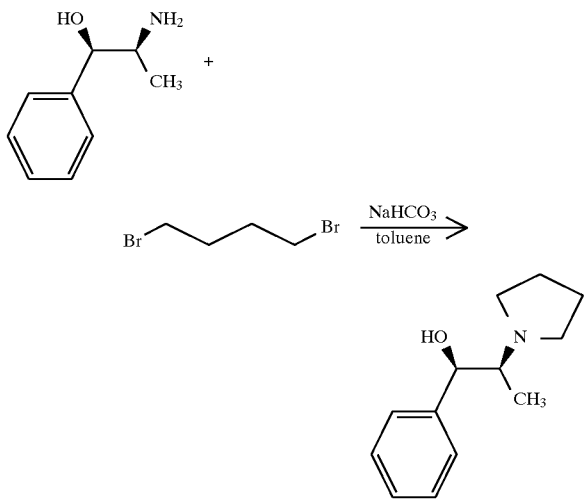

Step A: Preparation of [R-(R*,S*)]-β-methyl-α-phenyl-1-pyrrolidineethanol

Under nitrogen, to a 22 L three-necked round bottom flask equipped with a mechanical stirrer, a condenser with Dean-Stark trap and a thermocouple was charged with toluene (8 L), (1R,2S)-(−)-norephedrine (1.512 kg, 10 mol), 1,4-dibromobutane (2.375 kg, 11 mol) and sodium bicarbonate (1.848 kg, 22 mol) (note 1). The solid-liquid heterogeneous reaction mixture was then heated under reflux with stirring. The batch was kept under reflux at 105°–118° C. (note 2) until the completion of the reaction (note 3). There was 360 mL water collected in the Dean-Stark trap by the end of the reaction (note 4).

The batch was cooled to ambient temperature, filtered through a sintered glass funnel to remove solid sodium bromide salt. The wet cake was washed with 3 L toluene. The combined filtrate and wash was washed with water (6 L). The organic layer was then concentrated at a reduced pressure to a volume of about 5 L (about ⅓ of the original total volume) (note 5).

Notes 1. (1R,2S)-(−)-Norephedrine and 1,4-dibromobutane were purchased from Alps Pharmaceutical Co. and Leeds Chemical Co. respectively. For the small scale reaction (250 g or less) these two compounds were purchased from Aldrich Chemical Co.

2. The reflux temperature was gradually increased as the reaction progressed.

3. The reaction normally took 18–22 h to complete. It was monitored by HPLC assay. An HPLC sample of the reaction was prepared as follows: 50 μL filtered clear reaction solution (Whatman syringe filter 0.45 μM PTFE) was dissolved in MeCN to 50 mL. The ratio of the product to starting material (1R,2S )-(−)-norephedrine HPLC area percentage should be 99:1 or higher at the end of the reaction.

HPLC conditions: HPLC Column: 4.6 mm×25 cm Inertsil phenyl Eluent A: MeCN; Eluent B: pH 6.0 phosphate buffer, 15 mM (8.28 g $NaH_2PO_4.H_2O$ and 0.8 mL $Et_3N$ in 4 L HPLC grade water); Gradient: 14% A kept for 5 min then changed to 44% A over 11 min and kept this ratio for another 6 min; Injection: 20 μL; Flow rate: 1.5 mL/min; Detection: 210 nm; Temperature: 23° C.; and Retention Times: Sodium bromide: 1.8 min; Norephedrine: 5.0 min; Product: 12.0 min; Toluene: 22.5 min.

4. Water started to generate soon after the batch began to reflux. It was mostly removed by the Dean-Stark trap with toluene-water azeotropic distillation. In this case 360 mL water was distilled out which was exact the theoretical amount. The presence of small amount water was essential to the reaction, however, if there was too much water stayed in the reaction mixture it would mix with inorganic salt and formed sticky, wet solid lump at the bottom of the flask which could be a potential problem for stirring and subsequent filtration.

5. The main purpose here is to remove most of the water in the toluene solution because the water in toluene solution would interfere the HCl salt formation, lowering the recovery of the salt product.

Step B: Preparation of [R-(R*,S*)]-β-methyl-α-phenyl-1-pyrrolidineethanol hydrochloride The batch volume of the organic layer from Step A was then adjusted to 10 L with toluene and cooled to 10°–15° C. with ice-water bath. HCl in IPA (2.56 L, 4.3N) was added to the toluene solution slowly over a period of about 50 minutes, keeping the batch temperature below 25° C. (note 6). The batch was aged at ambient temperature for 1 h and isopropyl alcohol was removed by azeotropic distillation (Note 7). The batch was flushed with toluene (2×2 L) until the concentration of the product in supernatant was less than 3 g/L. The batch was then cooled to 15° C. and aged at this temperature for 1 h. The HCl salt was isolated by filtration and the wet cake was washed with toluene (2×2.5 L). The product loss in combined filtrate and wash was less than 1%.

Notes

6. Formation of HCl salt was necessary to remove non-amine organic components such as 1,4-dibromobutane which is known to decrease the enantioselectivity of the subsequent chiral addition reaction.

7. To increase the HCl salt product isolation yield removal of isopropyl alcohol (IPA) was necessary due to the high solubility of HCl salt in the presence of IPA.

Step C: Isolation of [R-(R*,S*)]-β-methyl-α-phenyl-1-pyrrolidineethanol

[R-(R*,S*)]-β-methyl-α-phenyl-1-pyrrolidineethanol hydrochloride, a semi-dried wet cake isolated in Step B (Note 8) was transferred to a mixture of 6 L toluene and 5.5 L of 2.0N NaOH. Two phases were well mixed and layers were separated. The aqueous layer (pH>12) was extracted with toluene (4 L). The combined organic layers were washed with deionized water (3 L), then concentrated and flushed with toluene (5 L). The final batch volume was adjusted to about 5 L. The final solution gave [R-(R*,S*)]-β-methyl-α-phenyl-1-pyrrolidineethanol (1.97 kg) in toluene as a light yellow solution (45 wt %) in 96% yield (note 9). The solution KF was 80–100 μg/mL.

$^1$H NMR (300 MHz, $CDCl_3$) δ: 0.80 (d, 3H, J=6.7), 1.82 (m, 4H), 2.49 (m, 1H), 2.64 (m, 2H), 2.80 (m, 2H), 3.64 (s, 1H), 5.01 (d, 1H, J=3.1), 7.25 (m, 1H), 7.34 (m, 4H).

$^{13}$C NMR (75.5 MHz, $CDCl_3$) δ: 12.1, 23.6, 51.9, 65.5, 72.7, 125.9, 126.7, 128.0, 141.9.

Notes

9. Alternatively, [R-(R*,S*)]-β-methyl-α-phenyl-1-pyrrolidineethanol may be isolated as a solid free base (m.p. 44°–45° C.) by removing all solvent.

EXAMPLE 2

[R-(R*,S*)]-β-methyl-α-phenyl-1-pyrrolidineethanol

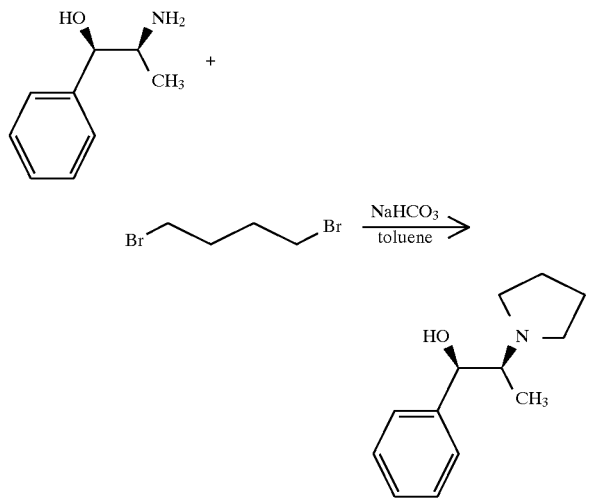

Step A: Preparation of [R-(R*,S*)]-β-methyl-α-phenyl-1-pyrrolidineethanol

Under nitrogen, to a 2 L three-necked round bottom flask equipped with a mechanical stirrer, a condenser with Dean-Stark trap and a thermocouple was charged with toluene (800 mL), (1R,2S)-(–)-Norephedrine (159.8 g, 1.057 mol), 1, 4-dibromobutane (251 g, 1.162 mol) and sodium bicarbonate (177.6 g, 2.114 mol). The solid-liquid heterogeneous reaction mixture was then heated to reflux with stirring. The batch was kept under reflux at 110°–118° C. until the completion of the reaction.

Water started to generate soon after the batch began to reflux. It was mostly removed (usually 90–95% of total water formed during the reaction) by the Dean-Stark trap with toluene-water azeotropic distillation. The presence of small amount water was essential to the reaction, however, if there was too much water stayed in the reaction mixture it would mix with inorganic salt and formed sticky, wet solid lump at the bottom of the flask which was a potential problem for stirring and subsequent filtration.

The reaction was monitored by HPLC. It normally took 18–22 h to complete. There was 36 mL water (total amount is 38 mL, 2.1 mol in this reaction) collected in the Dean-Stark trap.

HPLC sample preparation: 50 μL filtered clear reaction solution (Whatman syringe filter 0.45 μM PTFE) was dissolved in 50/50 MeCN/water to 50 mL. The ratio of the product to starting material norephedrine HPLC area percentage should be around 94.5:5.5 or higher. The level of 1,4-dibromobutane (the ratio to product should be less than 0.8 mole %) could be determined by proton NMR or GC (GC method hasn't been developed yet).

HPLC conditions: Column: 4.6 mm×25 cm Inertsil phenyl; Eluent A: MeCN; Eluent B: pH6.0 phosphate buffer, 15 mM (8.28 g NaH$_2$PO$_4$.H$_2$O and 0.8 mL Et$_3$N in 4 L HPLC grade water); Gradient: 14% A kept for 5 min then changed to 44% A over 11 min and kept this ratio for another 6 min; Injection: 20 μL; Flow rate: 1.5 mL/min; Detection: 210 nm; Temperature: 23° C.; Retention Times: Sodium bromide 1.8 min., Norephedrine 5.0 min., Product, 12.0 min., Toluene 22.5 min.

The batch was cooled to ambient temperature, filtered through a sintered glass funnel to remove solid sodium bromide salt. The wet cake was washed with 300 mL toluene. The combined filtrate and wash was washed with D.I. water 2×400 mL. The top organic layer was then concentrated on a rotavap to around 400 mL (⅓ of the original total volume).

Step B: Preparation of [R-(R*,S*)]-β-methyl-α-phenyl-1-pyrrolidineethanol Hydrochloride The batch was then transferred back to the reaction flask and adjusted to 800 mL with toluene. It was cooled to 10°–15° C. with ice-water bath and HCl in IPA (260 mL, 4.5N) was added slowly in 30 min while kept the batch temperature below 25° C. The batch was aged at 23° C. for 1 h and solvent was removed by azeotropic distillation. About 200 mL distillate was out and 200 mL toluene was added meanwhile. When the product in supernatant concentration was less than 3 g/L cooled the batch to 15° C. The HCl salt was isolated by filtration and the wet cake was washed with toluene 2×250 mL. The product loss in combined filtrate and wash was less than 1%.

Step C: Isolation of [R-(R*,S*)]-β-methyl-α-phenyl-1-pyrrolidineethanol

The wet cake was transferred to a separatory funnel, 800 mL toluene and 700 mL 1.5N NaOH were added (no obvious exothermic observed). Two phases were mixed well and layers were separated. The aqueous layer (pH>12) was extracted with toluene 2×500 mL. The combined organic layer was concentrated on a rotavap and flushed with toluene 1×500 mL. The final batch volume was adjusted to about 500 mL. The final solution gave [R-(R*,S*)]-β-methyl-α-phenyl-1-pyrrolidineethanol (212 g) in toluene as a light yellow solution (45 wt %) with 95% yield. (The enatioselectivity of [R-(R*,S*)]-β-methyl-α-phenyl-1-pyrrolidineethanol determined to be about 95+% ee when the solution was used in the chiral addition of cyclopropyl acetylide to the PMB-protected ketoaniline.) The solution KF was 80–100 μg/mL.

EXAMPLES 3–9

[R-(R*,S*)]-β-methyl-α-phenyl-1-pyrrolidineethanol

Following the procedure described in Example 1 using the bases and solvents listed in the table below the desired producted was isolated in the yield indicated.

| Example No. | Base/Solvent | Temperature (°C.) | Yield |
|---|---|---|---|
| 3 | Aq. K$_2$CO$_3$/BuOH | 95 | 80% |
| 4 | 5 N NaOH/Toluene | 93 | 87% |
| 5 | NaHCO$_3$/THF | 67 | 90% |
| 6 | Na$_2$CO$_3$/NaHCO$_3$/NaI/Toluene (1.0:1.0:0.05) | 110 | 80% |
| 7 | 5N NaOH/THF | 65 | 91% |
| 8 | NaHCO$_3$/Heptane | 95 | 76% |
| 9 | 5 N NaOH/Heptane | 88 | 82% |

EXAMPLE 10

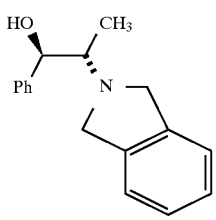

Following the procedure described in Example 1 using α,α'-dibromo-o-xylene and (1R,2S)-norephedrine the titled compound was prepared in a 93% yield.

$^1$H NMR (300 MHz, CDCl$_3$) δ: 7.43-7.36 (m, 4H), 7.32-7.25 (m, 5H), 5.11 (d, 1H), 4.21 (d, 2H), 4.05 (d, 2H), 3.62 (s, br, 1H), 2.90 (m, 1H), 0.95 (d, 3H).

EXAMPLE 11

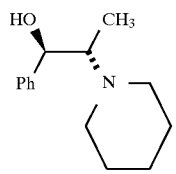

Following the procedure described in Example 1 using 1,5-dibromopentane and (1R,2S)-norephedrine the titled compound was prepared in a 98% yield.

$^1$H NMR (300 MHz, CDCl$_3$) δ: 7.38-7.20 (m, 5H), 5.0 (d, 1H), 3.58 (s, br, 1H), 2.69 (m, 2H), 2.56 (m, 2H), 2.48 (m, 1H), 1.82 (m, 6H), 0.80 (d, 3H).

EXAMPLE 12

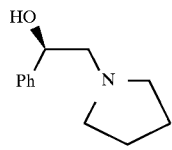

Following the procedure described in Example 1 using 1,4-dibromobutane and (2R)-2-hydroxy-2-phenylethylamine the titled compound was prepared in a 97% yield. (See A. I. Meyer, J. Org. Chem, 1980, 45, 2790, for the synthesis of (2R)-2-hydroxy-2-phenylethylamine.)

$^1$H NMR (300 MHz, CDCl$_3$) δ: 7.42-7.23 (m, 5H), 4.72 (dd, 1H), 4.0 (s, br, 1H), 2.83 2.74 (m, 3H), 2.58-2.45 (m, 3H), 1.80 (m, 4H).

EXAMPLE 13

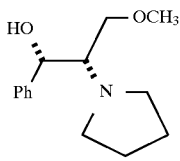

Following the procedure described in Example 1, using 1,4-dibromobutane and (1S,2S)-(+)-2-amino-2-methoxy-1-phenyl-1-propanol the titled compound was prepared in a 92% yield.

$^1$H NMR (300 MHz, CDCl$_3$) δ: 7.42-7.24 (m, 5H), 4.45 (d, 1H), 3.48-3.27 (m, 2H), 3.18 (s, 3H), 3.02.74 (m, 5H), 1.80 (m, 4H).

EXAMPLE 14

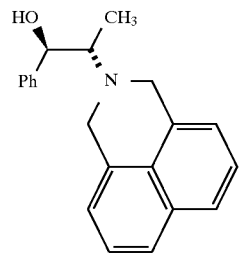

Following the procedure described in Example 1 using 1,8-bis(bromomethyl)naphthalene and (1R,2S)-norephedrine, the titled compound was prepared in a 81% yield.

$^1$H NMR (300 MHz, CDCl$_3$) δ: 7.75 (d, 2H), 7.45 (t, 2H), 7.32-7.21 (m, 7H), 5.17 (d, 1H), 4.28 (s, 4H), 3.02 (m, 1H), 1.0 (d, 3H).

EXAMPLE 15

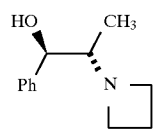

Following the procedure described in Example 1 using 1,3-dibromopropane and (1R,2S)-norephedrine the titled compound was prepared in a 96% yield.

$^1$H NMR (300 MHz, CDCl$_3$) δ: 7.34-7.15 (m, 5H), 7.43 (d, 1H), 3.48-3.20 (m, 4H), 2.47 (m, 1H), 2.37 (s, 1H), 2.08 (m, 2H), 0.64 (d, 3H).

EXAMPLE 16

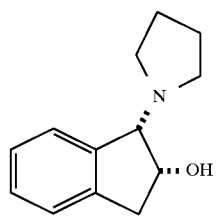

Following the procedure described in Example 1 using 1,4-dibromobutane and (1S,2R)-1-amino-2-indanol the titled compound can be prepared.

EXAMPLE 17

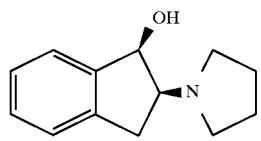

Following the procedure described in Example 1 using 1,4-dibromobutane and (1R,2S)-2-amino-1-indanol the titled compound can be prepared. (See E. J. Corey, et al, Tetrahedron Lett, 1993, 34, 52, and A. Mitrochkine, et al, Tetrahedron: Asymmetry, 1995, 6, 59, for the synthesis of (1R,2S)-2-amino-1-indanol.)

EXAMPLE 18

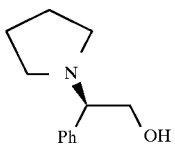

Following the procedure described in Example 1 using 1,4-dibromobutane and (2R)-2-amino-2-phenylethanol the titled compound can be prepared. (2R)-2-amino-2-phenylethanol can be prepared by reducing the commerically available (R)-(−)-phenylglycine.

EXAMPLE 19

(1R,2S)-N-Pyrrolidinyl Norephedrine

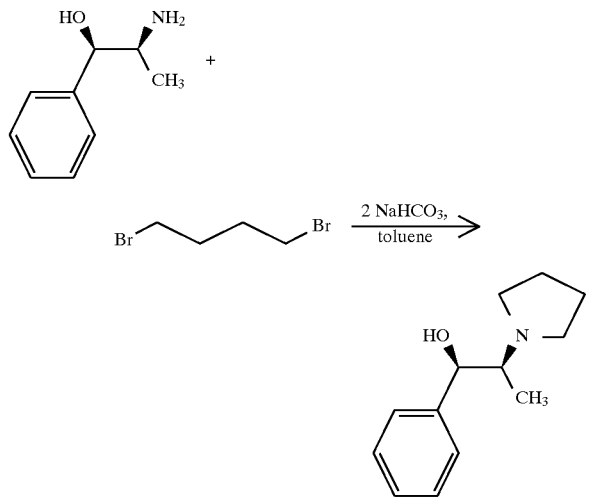

| Materials | mw | amount | mol. | equiv. |
|---|---|---|---|---|
| (1R,2S)-(−)-Norephedrine, 99% | 151.21 | 1.512 kg | 10 | 1.0 |
| 1,4-Dibromobutane, 99% | 215.93 | 2.375 kg | 11 | 1.1 |
| Sodium bicarbonate | 84.01 | 1.848 kg | 22 | 2.2 |
| Toluene | | 8 + 19 L | | |
| Citric acid | 192.12 | 2.882 kg | 15 | 1.5 |
| D.I. Water | | 16 L | | |
| Sodium hydroxide, 50 w/w % | 40.00 | 3.57 kg | 44.6 | 4.46 |
| Product Theory | | | | |
| (1R,2S)-(−)-N-Pyrrolidinyl norephedrine (HCl salt) | 205.3 (241.76) | 2.053 kg | 10 | 1.0 |

Under nitrogen, to a 22 L three-necked round bottom flask equipped with a mechanical stirrer, a condenser with Dean-Stark trap and a thermocouple was charged with toluene (8 L), (1R,2S)-(−)-Norephedrine (1.512 kg, 10 mol), 1,4-dibromobutane (2.375 kg, 11 mol) and sodium bicarbonate (1.848 kg, 22 mol). The solid-liquid heterogeneous reaction mixture was then heated to reflux with stirring. The batch was kept under reflux at 110°–118° C. until the completion of the reaction.

Water started to generate soon after the batch began to reflux. It was mostly removed (usually 90–95% of total water formed during the reaction) by the Dean-Stark trap with toluene-water azeotropic distillation. The presence of small amount water was essential to the reaction, however, if there was too much water stayed in the reaction mixture it would mix with inorganic salt and formed sticky, wet solid lump at the bottom of the flask which was a potential problem for stirring and subsequent filtration. The reaction was monitored by HPLC. It normally took 18–22 h to complete. There was 360 mL water (the theoretical total amount is 360 mL, 20 mol in this reaction) collected in the Dean-Stark trap.

HPLC sample preparation: 50 µL filtered clear reaction solution (Whatman syringe filter 0.45 µM PTFE) was dissolved in 50/50 MeCN/water to 50 mL. The ratio of the product to starting material norephedrine HPLC area percentage should be 99:1 or higher.

HPLC Conditions: Column: 4.6 mm×25 cm Inertsil phenyl; Eluent A: MeCN; Eluent B: pH6.0 phosphate buffer [15 mM (8.28 g $NaH_2PO_4.H_2O$ and 0.8 mL $Et_3N$ in 4 L HPLC grade water)]; Gradient: 14% A kept for 5 min then changed to 44% A over 11 min and kept this ratio for another 6 min; Injection: 20 µL; Flow rate: 1.5 mL/min; Detection: 210 nm; and Temperature: 23° C.

Retention Times: Sodium bromide 1.8 min; Norephedrine 5.0 min; Product 12.0 min; and Toluene 22.5 min.

The batch was cooled to ambient temperature, filtered through a sintered glass funnel to remove solid sodium bromide salt. The wet cake was washed with 3 L toluene. The combined filtrate and wash was washed with D.I. water 1×6 L (the product in aqueous layer loss was less than 1%).

The organic layer was transferred to a 50 L extractor and extracted with 30% aqueous citric acid solution at room temperature. The mixture was stirred for 15 min and the layers were separated.

The aqueous layer was transferred back to the extractor which contained 10 L toluene. 50 w/w % NaOH (3.57 kg) was added slowly so that the temperature was kept below 30° C. The mixture was stirred for 15 min and the layers were separated. (the pH of the aqueous layer was 12–12.5). The aqueous layer was extracted with toluene once (1×5 L). The aqueous layer was removed and combined organic layers were washed with D.I. water twice (2×5 L).

The washed organic layer was concentrated with vacuum and the batch volume was reduced to about 6–8 L. The batch was then flushed with toluene 2×3 L. The final batch volume was adjusted to about 5 L which gave the product (1.97 kg) in toluene as a light yellow solution (38 wt %) with 96% yield. The solution KF was 80–100 µg/mL.

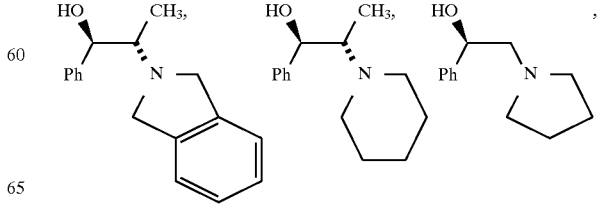

-continued
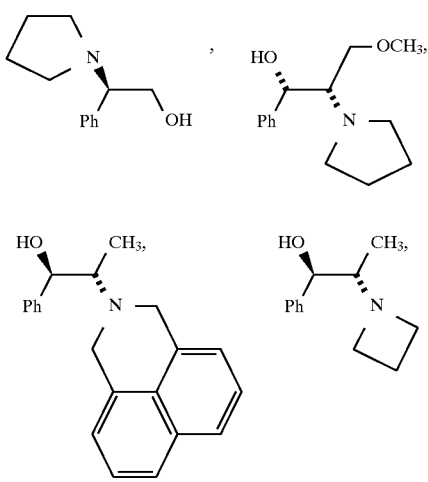
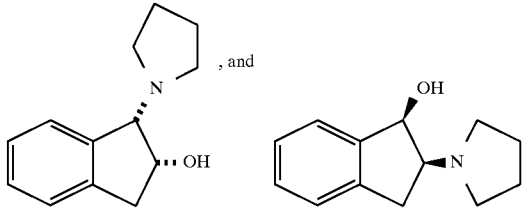
32. The process as recited in claim 30, wherein the compound of Formula I is:
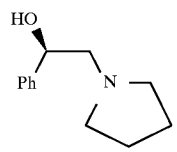

What is claimed is:

1. A process for the preparation of a hydrochloride salt of a compound of Formula I:

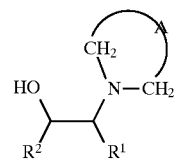

wherein

A represents:

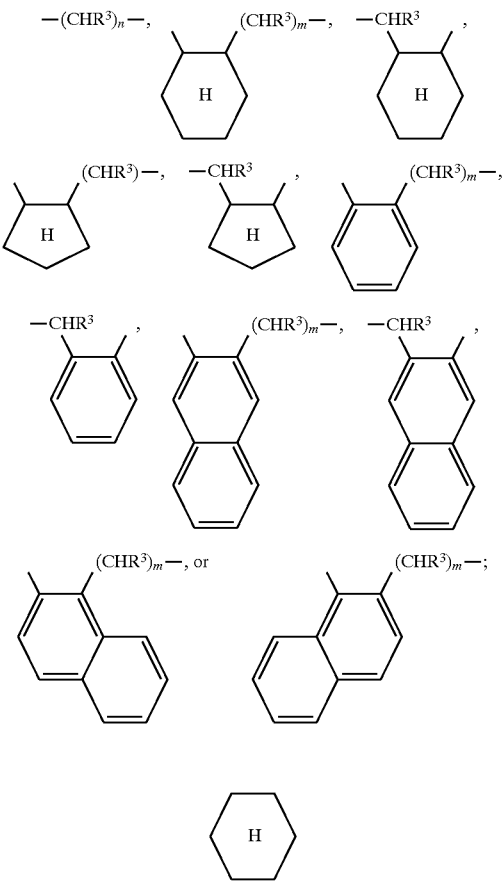

represents a six-membered ring, unsaturated or saturated, optionally substituted with one or two heteroatoms selected from N, O, or S, optionally substituted with $C_1$–$C_6$-alkyl;

represents: a five-membered ring, unsaturated or saturated, optionally substituted with one or two heteroatoms selected from N, O, or S, optionally substituted with $C_1$–$C_6$-alkyl;
n is 1, 2, or 3;
m is 0, or 1;
t is 0, 1, or 2;
s is 1 or 2;
$R^1$ is: H, phenyl, or $C_1$–$C_6$-alkyl, unsubstituted or substituted with $C_1$–$C_6$-alkoxy;
$R^2$ is: H, $C_1$–$C_6$-alkyl, or

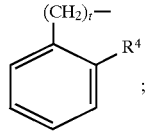

$R^3$ is: H, $C_1$–$C_6$-alkyl, or phenyl;
$R^4$ is: H, except that $R^1$ and $R^4$ can represent a carbon carbon bond, when t is 1 or 2, or —$(CH_2)_s$—, when t is 0;

comprising the steps of:

(a) refluxing the 1,2-amino alcohol compound,

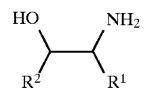

with an alkylating agent

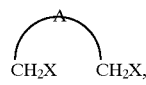

wherein X is Cl, Br, I, OTf, OTs or OMs; in the presence of a base and a solvent, at a reaction temperature of about 65° C. to about 120° C. for reaction time of about 12 to about 36 hours, while removing the water formed to give a solution of crude compound of Formula I;

(b) adding hydrogen chloride in solution or as a gas to a solution of the crude compound of Formula I at about 10° to about 15° C. and maintaining a reaction temperature of about 10° to about 25° C. to form a slurry of the hydrochloride salt of the compound of Formula I;

(c) azeotropically distilling the solvents leaving a concentrated slurry-solution of the hydrochloride salt of the compound of Formula I;

(d) crystallizing the concentrated solution of the hydrochloride salt of the compound of Formula I at about 0° C. to about 20° C. to give a slurry of crystalline hydrochloride salt of the compound of Formula I; and (e) filtering the slurry of crystalline hydrochloride salt of the compound of Formula I to isolate crystalline hydrochloride salt of the compound of Formula I.

2. The process as recited in claim 1, step (a), wherein the base is selected from the group consisting of: $Li_2CO_3$, $Na_2CO_3$, $K_2CO_3$, $LiHCO_3$, $NaHCO_3$, $KHCO_3$, LiOH, NaOH, and KOH.

3. The process as recited in claim 2, wherein the solvent is selected from the group consisting of: toluene, heptane, n-butanol, methylcyclohexane, and tetrahydrofuran.

4. The process as recited in claim 3, wherein aminoalcohol compound to dihalide ratio is about 1 to about 1.1 ratio.

5. The process as recited in claim 4, wherein the dihalide to base ratio is about 1 to about 2 ratio.

6. The process as recited in claim 5, wherein the base is selected from the group consisting of: $KHCO_3$, $NaHCO_3$, $K_2CO_3$, and $Na_2CO_3$.

7. The process as recited in claim 6, wherein the solvent is toluene.

8. The process as recited in claim 7, wherein the reaction temperature is about 105° to about 118° C.

9. The process as recited in claim 8, wherein the reaction time is about 18 to about 24 hours.

10. The process as recited in claim 9, wherein the compound of formula I is selected from the group consisting of:

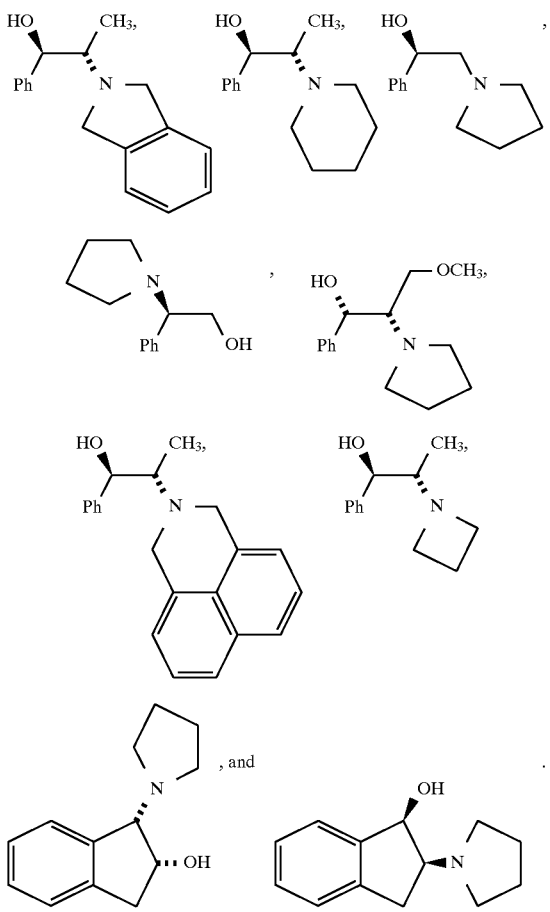

, and

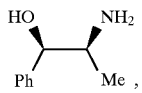

11. A process for the preparation of [R-(R*,S*)]-β-methyl-α-phenyl-1-pyrrolidineethanol hydrochloride or its enantiomer,

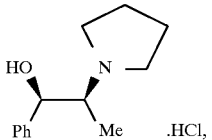

comprising the steps of:
(a) refluxing (1R,2S)-(−)-norephedrine or its enantiomer,

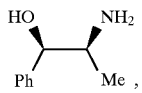

with 1,4-dibromobutane in the presence of a base, sodium bicarbonate and a solvent, toluene, at a reaction temperature of about 100° to about 120° C. for reaction time of about 12 to about 24 hours, while removing the water formed to give a toluene solution of crude [R-(R*,S*)]-β-methyl-α-phenyl-1-pyrrolidineethanol or its enantiomer;
(b) adding a solution of hydrogen chloride in isopropanol to a toluene solution of [R-(R*,S*)]-β-methyl-α-phenyl-1-pyrrolidineethanol or its enantiomer at about 10° to about 15° C. and maintaining a reaction temperature of about 10° to about 25° C. to form [R-(R*,S*)]-β-methyl-α-phenyl-1-pyrrolidineethanol hydrochloride or its enantiomer;

(c) azeotropically distilling the isopropanol-toluene leaving a concentrated toluene slurry of [R-(R*,S*)]-β-methyl-α-phenyl-1-pyrrolidineethanol hydrochloride or its enantiomer;

(d) crystallizing the concentrated toluene slurry of ([R-(R*,S*)]-β-methyl-α-phenyl-1-pyrrolidineethanol hydrochloride or its enantiomer at about 0° C. to about 20° C. to give a toluene slurry of crystalline [R-(R*,S*)]-β-methyl-α-phenyl-1-pyrrolidineethanol hydrochloride or its enantiomer; and (e) filtering the toluene slurry of crystalline [R-(R*,S*)]-β-methyl-α-phenyl-1-pyrrolidineethanol hydrochloride or its enantiomer to isolate crystalline [R-(R*,S*)]-β-methyl-α-phenyl-1-pyrrolidineethanol hydrochloride or its enantiomer.

12. The process as recited claim 11, wherein (1R,2S)-(−)-norephedrine to 1,4-dibromobutane ratio is about a 1 to about 1.1 ratio.

13. The process as recited claim 12, wherein the 1,4-dibromobutane to NaHCO₃ is about a 1 to about 2 ratio.

14. The process as recited claim 13, wherein the reaction temperature is about 105° to about 118° C.

15. The process for the preparation of [R-(R*,S*)]-β-methyl-α-phenyl-1-pyrrolidineethanol or its enantiomer comprising the steps as recited in claim 14 and the following additional steps:

(a) neutralizing [R-(R*,S*)]-β-methyl-α-phenyl-1-pyrrolidineethanol hydrochloride or its enantiomer with aqueous NaOH in toluene producing a biphasic solution containing [R-(R*,S*)]-β-methyl-α-phenyl-1-pyrrolidineethanol or its enantiomer;

(b) extracting [R-(R*,S *)]-β-methyl-α-phenyl-1-pyrrolidineethanol or its enantiomer into a toluene-organic layer; and (c) concentrating the [R-(R*,S*)]-β-methyl-α-phenyl-1-pyrrolidineethanol or its enantiomer containing toluene-organic layer to give solid [R-(R*,S*)]-β-methyl-α-phenyl-1-pyrrolidineethanol or its enantiomer.

16. A compound of Formula I:

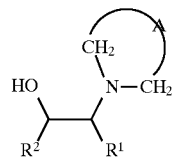

or its enantiomer, wherein

A represents:

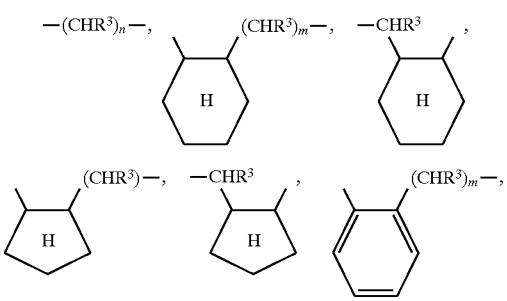

-continued

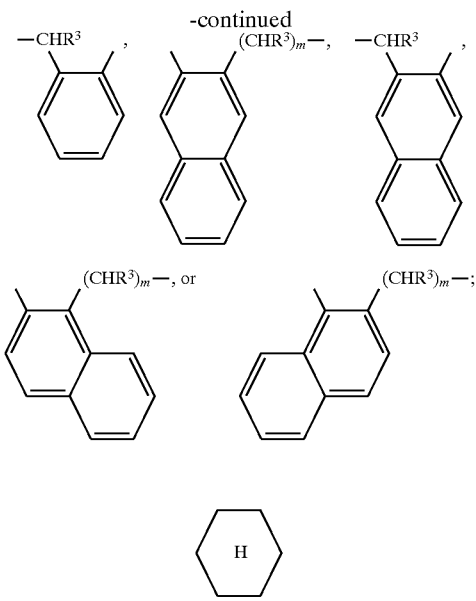

represents a six-membered ring, unsaturated or saturated, optionally substituted with one or two heteroatoms selected from N, O, or S, optionally substituted with $C_1$–$C_6$-alkyl;

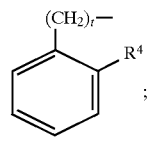

represents: a five-membered ring, unsaturated or saturated, optionally substituted with one or two heteroatoms selected from N, O, or S, optionally substituted with $C_1$–$C_6$-alkyl;

n is 1, 2, or 3;
m is 0, or 1;
t is 0, 1, or 2;
s is 1 or 2;
$R^1$ is: H, phenyl, or $C_1$–$C_6$-alkyl, unsubstituted or substituted with $C_1$–$C_6$-alkoxy;
$R^2$ is: H, $C_1$–$C_6$-alkyl, or

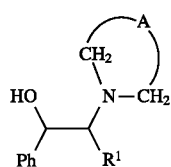

$R^3$ is: H, $C_1$–$C_6$-alkyl, or phenyl; and
$R^4$ is: H, except that $R^1$ and $R^4$ can represent a carbon carbon bond, when t is 1 or 2, or —$(CH_2)_s$—, when t is 0, with the proviso that:
(a) when the compound of structural formula I

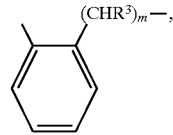

or its enantiomer is defined as $R^1$ is H or $CH_3$, that A cannot represent —$(CHR^3)_n$—, or

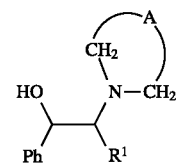

when n is 2, or 3, $R^3$ is H and m is 0; and (b) when the compound of structural formula I or its enantiomer is defined as

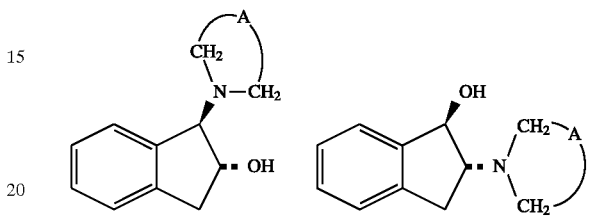

that A cannot represent —$(CHR^3)_n$—, when n is 2, and $R^3$ is H, as a free base or an acid salt thereof.

17. A process for the preparation of a compound of Formula I:

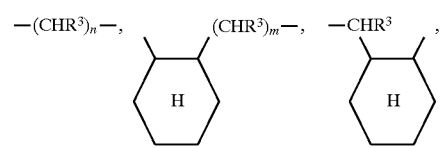

wherein

A represents:

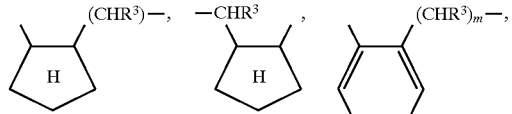

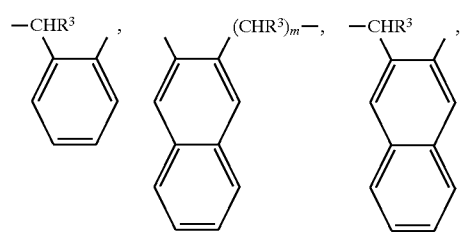

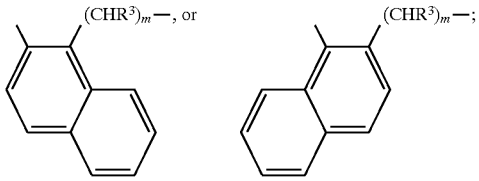

represents a six-membered ring, unsaturated or saturated, optionally substituted with one or two heteroatoms selected from N, O, or S, optionally substituted with $C_1$–$C_6$-alkyl;

represents: a five-membered ring, unsaturated or saturated, optionally substituted with one or two heteroatoms selected from N, O, or S, optionally substituted with $C_1$–$C_6$-alkyl;
n is 1, 2, or 3;
m is 0, or 1;
t is 0, 1, or 2,
s is 1 or 2;
$R^1$ is: H, phenyl, or $C_1$–$C_6$-alkyl, unsubstituted or substituted with $C_1$–$C_6$-alkoxy;
$R^2$ is: H, $C_{-C6}$-alkyl, or

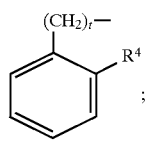

$R^3$ is: H, $C_1$–$C_6$-alkyl, or phenyl;
$R^4$ is: H, except that $R^1$ and $R^4$ can represent a carbon carbon bond, when t is 1 or 2, or —$(CH_2)_s$—, when t is 0;
comprising the steps of:
(a) refluxing the 1,2-amino alcohol compound,

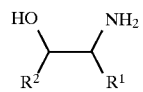

with an alkylating agent

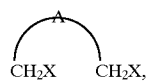

wherein X is Cl, Br, I, OTf, OTs or OMs; in the presence of a base and a solvent at a reaction temperature of about 100° to about 120° C. for reaction time of about 12 to about 36 hours, while removing the water formed to give a solution of crude compound of Formula I;
(b) filtering the solvent solution containing the crude compound of Formula I to remove the sodium bromide salt, once the solution reaches room temperature;
(c) washing the sodium bromide wet cake with a solvent;
(d) extracting the filtrate-solvent solution containing the crude compound of Formula I with water to remove any additional sodium bromide salt;
(e) mixing the washed filtrate-solvent solution containing the crude compound of Formula I with an aqueous acid solution to form the acid salt of the compound of Formula I;
(f) isolating the aqueous layer containing the acid salt of a compound of Formula I;
(g) neutralizing a biphasic solution of the aqueous layer containing the acid salt of a compound of Formula I and solvent with a base while maintaining the temperature below about 30° C.;
(h) extracting the compound of Formula I from the biphasic solution into the solvent after mixing for less than about one hour; and
(i) isolating the solvent layer containing the compound of Formula I.

18. The process as recited in claim 17, steps (a) and (g), wherein the base used in each step is independently selected from the group consisting of: $Li_2CO_3$, $Na_2CO_3$, $K_2CO_3$, $LiHCO_3$, $NaHCO_3$, $KHCO_3$, LiOH, NaOH, and KOH.

19. The process as recited in claim 18, steps (a), (c) and (g), wherein the solvent is selected from the group consisting of: toluene, heptane, n-butanol, methylcyclohexane, and tetrahydrofuran.

20. The process as recited in claim 19, step (e) wherein the aqueous acid solution is selected from the group consisting of: an aqueous inorganic acid solution and an aqueous organic acid solution.

21. The process as recited in claim 20, step (a) wherein aminoalcohol compound to dihalide ratio is about 1 to about 1.1 ratio.

22. The process as recited in claim 21, step (a) wherein the dihalide to base ratio is about 1 to about 2 ratio.

23. The process as recited in claim 22, step (a) wherein the base is selected from the group consisting of: $KHCO_3$, $NaHCO_3$, $K_2CO_3$, and $Na_2CO_3$.

24. The process as recited in claim 23, step (e) wherein the aqueous acid solution is an aqueous inorganic acid solution selected from the group consisting of: HCl, HBr, $H_3PO_4$ and $H_2SO_4$.

25. The process as recited in claim 23, step (e) wherein the aqueous acid solution is an aqueous organic acid solution selected from the group consisting of: citric acid, acetic acid, trifluoroacetic acid, maleic acid, methylsulfonic acid, p-toluenesulfonic acid, formic acid, and benzoic acid.

26. The process as recited in claim 25, steps (a), (c) and (g) wherein the solvent is toluene.

27. The process as recited in claim 26, step (a) wherein the reaction temperature is about 105° to about 118° C.

28. The process as recited in claim 27, step (a) wherein the reaction time is about 18 to about 24 hours.

29. The process as recited in claim 28, step (e) wherein the aqueous acid solution is citric acid.

30. The process as recited in claim 29, step (g) wherein the base is selected from the group consisting of: aqueous LiOH, KOH and NaOH.

31. The process as recited in claim 30, wherein the compound of Formula I is selected from the group consisting of: